May 15, 1934. W. G. BATE Plant Pat. 97
ROSE
Filed Jan. 28, 1933
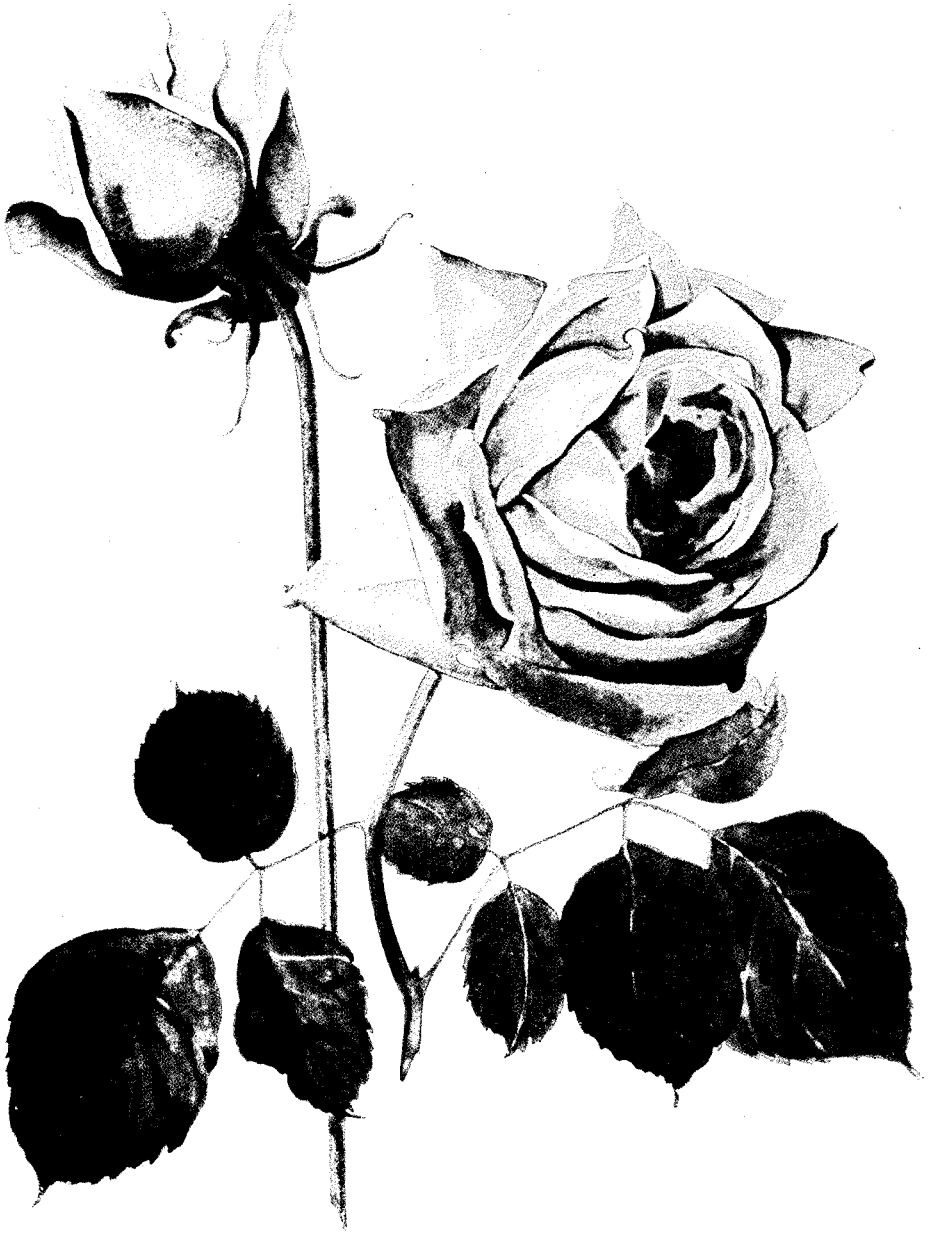
INVENTOR
Warwick G. Bate
By Frank S. Greene
ATTORNEY Patented May 15, 1934

Plant Pat. 97

UNITED STATES PATENT OFFICE

97

ROSE

Warwick G. Bate, Newton Falls, Ohio

Application January 28, 1933, Serial No. 653,949

1 Claim. (Cl. 47—61)

This discovery relates to a new variety of hybrid tea rose which appeared as a sport of the well known Francis Scott Key rose.

The new variety of rose discovered and propagated by me is a large sized rose of dark red color, similar in appearance to the Francis Scott Key rose, having ovate petals which curl back at the edges as the petals open so that each petal forms straight sides converging to a point at its tip.

The new variety, however, has several individual variations from the parent rose. Its color is of a somewhat deeper shade of red, the number of its petals is considerably less, and when grown in hothouses during the winter months it opens more freely and uniformly and retains its color more permanently.

The Francis Scott Key rose is highly regarded by florists by reason of the large size and beauty of the flower, the excellent keeping qualities of the cut flowers and their ability to withstand rough usage without damage. The Francis Scott Key rose can be advantageously grown only during the summer months, due to the fact that when grown in the shorter days of the winter months the petals tend to "ball" and "blue". By "ball" is meant the tendency of the inner petals of the flower to cling together in the form of a ball instead of opening evenly; and by "blue" is meant the tendency of the petals to quickly fade to a bluish color.

The new variety of rose discovered and propagated by me is in appearance quite similar to the summer grown roses of the Francis Scott Key variety, and possesses the same advantages of ruggedness and superior keeping qualities.

One of the main advantages of the new variety is that it is a practical rose for winter growing, since it does not have the tendency to "ball" or "blue" when grown during the winter months.

Since the discovery of the sport, I have succeeded in propagating the new variety and in making permanent the advantageous characteristics of the original sport plant, and have at the present time a large number of rose plants of the new variety which are producing, during the winter months, the flowers herein illustrated and described.

The accompanying illustrations show in full color a partially open flower and a more fully open flower of my new variety.

The petals of my new variety of rose are similar in size and shape to those of the summer grown Francis Scott Key rose, and the color of the petals is very nearly the same, being, however, a slightly deeper shade of red. The new rose, however, has a smaller number of petals than the Francis Scott Key rose. The Francis Scott Key rose has from 65 to 75 petals, whereas the new variety has only from 40 to 55 petals. Probably by reason of the fact that this new variety has fewer petals, there is less tendency for the petals to cling together and the buds open more uniformly without any tendency to ball, with the result that the inner petals of the flower are of more perfect shape.

The leaves of my new variety of rose are dark green, glossy and slightly cupped. The bark and twigs are green, with many reddish green thorns. The plant blooms freely and continuously.

The form of the bud is ovoid to globular, with almost circular petals evenly rolled back along the edges. The outwardly curled edges of the petals are straight and tapering when the flower opens.

There is very little difference in the color of the petals upon the inner and the outer surface, although as is usual with all red roses, the outer surface is somewhat lighter. Since color is not an intrinsic quality of any flower, the hue depends entirely upon the light in which it is viewed. In a rather cold north light without sunshine, the color of the petals is fairly well matched by Plate No. 43 of Koster's Color Guide published by A. T. De La Mare Company, Inc., New York city, in 1931, which is called Amaranth Red. Towards the base of the petals, shades of the more brilliant French Purple Plate No. 42 of the same Guide appear, but toward the outer edges of the petals shades of Crimson Carmine Plate No. 41 of the same work may be detected. The outer surfaces of the petals in the same light range through shades of Rosy Magenta Plate No. 44 and Violet Rose Plate No. 39 and Solferino Red Plate No. 40, the latter two indicating the highlights as they appear under such conditions.

Ridgeway's Color Chart lacks the whole range of Magenta Crimsons in which the tones of this flower lie. However, the colors Spinel Pink and Spinel Red Plate No. XXVI come close to matching the highlights and deeper tones respectively as the flowers are seen in an equal light.

When the flowers are brought nearer to the sun-light, the pitch of all these colors rises to a greater degree of brilliance.

Another very advantageous characteristic of the new variety is that the petals retain their deep red color after cutting and do not have a tendency to blue.

I have produced, therefore, a new variety of rose which produces flowers of large size and great beauty, which are not easily damaged by rough handling and which have superior keeping qualities, the new variety of rose being particularly well suited for winter forcing and producing flowers highly desirable for the winter cut flower trade.

I claim:

A rose plant such as that propagated from a sport of the Francis Scott Key rose and herein shown and described, which bears a flower having 40 to 55 petals of a deep red color, the individual petals of outer rows being characterized by substantially straight outwardly curled edges which taper at an acute angle to the tip of the petal when the flower has opened, said plant when grown under glass in the winter season producing a flower which opens freely and uniformly without balling or bluing.

WARWICK G. BATE.